United States Patent
Lomryd et al.

(10) Patent No.: US 7,094,545 B2
(45) Date of Patent: *Aug. 22, 2006

(54) PHARMACEUTICAL COMPOSITION AS SOLID DOSAGE FORM AND METHOD FOR MANUFACTURING THEREOF

(75) Inventors: Håkan Lomryd, Malmö (SE); Helena Nicklasson, Malmö (SE); Lars-Erik Olsson, Malmö (SE)

(73) Assignee: Ferring BV, Hoofddorp (NL)

( * ) Notice: Subject to any disclaimer, the term of this patent is extended or adjusted under 35 U.S.C. 154(b) by 370 days.

This patent is subject to a terminal disclaimer.

(21) Appl. No.: 10/425,993

(22) Filed: Apr. 30, 2003

(65) Prior Publication Data

US 2004/0220080 A1    Nov. 4, 2004

(51) Int. Cl.
*A61K 38/00*    (2006.01)

(52) U.S. Cl. .......................................................... 435/6
(58) Field of Classification Search ...................... 435/6
See application file for complete search history.

(56) References Cited

U.S. PATENT DOCUMENTS

| | | | |
|---|---|---|---|
| 4,675,188 A | 6/1987 | Chu | |
| 4,820,627 A | 4/1989 | McGeehan | |
| 5,047,398 A * | 9/1991 | Hagstam et al. | 514/15 |
| 2002/0122817 A1 | 9/2002 | Gabel et al. | |
| 2003/0091623 A1 * | 5/2003 | Cumming et al. | 424/465 |
| 2003/0091637 A1 | 5/2003 | Peterelt et al. | |
| 2003/0175214 A1 * | 9/2003 | Staniforth et al. | 424/46 |
| 2003/0185764 A1 * | 10/2003 | Staniforth et al. | 424/46 |

FOREIGN PATENT DOCUMENTS

| | | |
|---|---|---|
| EP | 0 752 877 B1 | 7/2000 |
| EP | 0 710 122 B1 | 12/2001 |
| EP | 1 255 557 A1 | 11/2002 |
| WO | WO 95/18602 | 7/1995 |
| WO | WO 97/15297 A | 5/1997 |
| WO | WO 97/15297 A1 | 5/1997 |
| WO | WO 97/23485 A1 | 7/1997 |
| WO | WO 97/48379 A1 | 12/1997 |
| WO | WO 98/10753 * | 3/1998 |
| WO | WO 98/10753 A1 | 3/1998 |
| WO | WO 00/9423 A | 10/2000 |
| WO | WO 00/59423 A1 | 10/2000 |
| WO | WO 01/78694 A2 | 10/2001 |
| WO | WO 01/78695 A2 | 10/2001 |
| WO | WO 01/78696 A2 | 10/2001 |
| WO | WO 01/82906 A1 | 11/2001 |
| WO | WO 02/00197 A1 | 1/2002 |
| WO | WO 03/094886 A2 | 11/2003 |

OTHER PUBLICATIONS

"Current Issues and Troubleshooting Fluid Bed Granulation", May 1998, Pharmaceutical Technology Europe, http://www.niroinc.com/html/pharma/phpdfs/niroreprint2.pdf.
"Pharmaceutical Dosage Forms: Tablets"; vol. 1, pp. 297-298, H.A. Lieberman et al., New York & Basel, 1989.
"Pharmaceutical Dosage Forms: Parenteral Medications", vol. 3, pp. 27-29, H.A. Lieberman et al., New York & Basel, 1990.
"Pharmaceutics—The Science of Dosage Form Design", pp. 625-627, M.E. Aulton et al., Edinburgh, London, Melbourne & New York, 1988.
"Handbook of Pharmacetical Excipients", Ed. A.H. Kibble, 3$^{rd}$ Ed., American Pharmaceutical Assocation, USAS and Pharmaceutical Press UK 2000.
N.A. Armstrong; "Tabletting", Pharmaceutics—The Science of Dosage Form Design, pp. 647-668, 1988.
Robert O. Williams III et al., "Compaction Properties of Microscrystalline Cellulose and Sodium Sulfathlazole in Combination with Talc or Magnesium Stearate", Journal of Pharmaceutical Sciences vol. 78, No. 12, Dec. 1989, pp. 1025-1034.
DMV International Product group overview for Pharmatose milled and sleved lactose.
DMV International Product group overview for Pharmatose DC lactose.
Hwang et al., "A Systematic Formulation Optimazation Process for a Generic Pharmaceutical Tablet," *Pharmaceutical Technology*, pp. 48-64, May 1998.
Fast Flo Lactose — technical sheet, Jun. 2001.
Handbook of Pharmaceutical Excipients, 3$^{rd}$ Edition, Edited by Arthur Kibbe, The Pharmaceutical Press, 2000, pp. 276-285.

* cited by examiner

*Primary Examiner*—Cecilia J. Tsang
*Assistant Examiner*—Maury Audet
(74) *Attorney, Agent, or Firm*—Foley & Lardner LLP

(57) ABSTRACT

The present invention relates to a novel pharmaceutical composition as a solid dosage form comprising desmopressin as a therapeutically active ingredient, and to a method for manufacturing thereof. The invention relates to a pharmaceutical composition as a solid dosage form comprising desmopressin, or a pharmaceutically acceptable salt thereof, as a therapeutically active ingredient together with a pharmaceutically acceptable excipient, diluent or carrier, or mixture thereof, wherein at least one of said excipient, diluent and carrier is a substance selected from a monosaccharide, disaccharide, oligosaccharide and a polysaccharide, wherein the said substance has an average particle size in the range of from 60 to 1,000 μm. A method according to the present invention provides an improved production of solid dosage forms of desmopressin.

15 Claims, No Drawings

US 7,094,545 B2

PHARMACEUTICAL COMPOSITION AS SOLID DOSAGE FORM AND METHOD FOR MANUFACTURING THEREOF

FIELD OF THE INVENTION

The present invention relates to a novel pharmaceutical composition as a solid dosage form comprising desmopressin as a therapeutically active ingredient, and to a method for manufacturing thereof.

TECHNICAL BACKGROUND

Desmopressin, also known as dDAVP, is the therapeutically active ingredient (as its acetate salt) in the pharmaceutical product Minirin®, which is marketed inter alia as a nasal spray and a tablet formulation. Desmopressin is primarily used in the treatment of primary nocturnal enuresis, i.e. bedwetting, in children, but it is approved also for the treatment of nocturia and diabetes insipidus. The first market introduction of the tablet formulation was in Sweden in 1987.

In short, a solid dosage form such as a tablet formulation is typically manufactured by compression of a suitable granulate to the desired solid dosage form, where the granulate is composed of the required constituents as a mixture of solid particles. Typical such particles are the therapeutically active ingredient, various excipients (fillers), disintegrating agents, lubricants and binders, optionally together e.g. with flavoring agent, preservative and/or colorant. The commercially available Minirin® tablet is prepared according to this general protocol, and the tablet was first disclosed as set forth in the patent U.S. Pat. No. 5,047,398, the teachings of which are incorporated herein by reference. For a comprehensive overview of pharmaceutical tablet manufacturing, see "Tableting" (by N. A. Armstrong) in "Pharmaceutics—The science of dosage form design", pp 647–668; Ed. M. E. Aulton, Churchill Livingstone, Edinburgh, London, Melbourne and New York, 1988, the entire teachings of which are incorporated herein by reference.

The Minirin® tablet that is currently marketed, and thus produced in industrial scale, consists of the therapeutically active ingredient desmopressin together with potato starch and lactose as excipients, and a suitable amount of binder and lubricant, respectively.

In any tablet compression of a granulate composed of a mixture of solid particles there is a general need to perform the compressing operation at the highest possible speed while at the same time minimising machine wear and obtaining tablets of a quality that meets the regulatory demands of all relevant territories.

DISCLOSURE OF THE INVENTION

It has now been discovered that a certain dimension of the excipient particles unexpectedly provides a substantial improvement on the speed of the manufacturing process, while both machine wear and tablet quality remain substantially unaltered compared to the industrial manufacturing process hitherto used. In essence, the dimension in question seems to affect the flowability of particles and granulate in such a manner that it provides an improved overall capacity, and hence speed, in the manufacturing process for the desmopressin tablet formulation.

More specifically, the present invention relates to a pharmaceutical composition as a solid dosage form comprising desmopressin, or a pharmaceutically acceptable salt thereof, as a therapeutically active ingredient together with a pharmaceutically acceptable excipient, diluent or carrier, or mixture thereof, wherein at least one of said excipient, diluent and carrier is a substance selected from a monosaccharide, disaccharide, oligosaccharide and a polysaccharide, wherein the said substance has an average particle size in the range of from 60 to 1 000 µm.

In those embodiments where there is a mixture of at least two of the aforementioned types of saccharides, at least one of them must accordingly be within the specified particle size range of the present invention.

In many cases the terms excipient, diluent and carrier can be used interchangeably, and they may even refer to one and the same substance, or to a mixture of similar such substances. The proper use and understanding of these terms is self-explanatory and lies well within the ability of a person skilled in the art of pharmaceutical formulation.

The pharmaceutical composition according to the present invention may optionally comprise at least one additive selected from a disintegrating agent, lubricant, binder, flavoring agent, preservative, colorant and a mixture thereof. Where considered suitable also other additives may be included. Representative examples of disintegrating agents, lubricants (e.g. magnesium stearate), binders (e.g. Kollidon® 25, BASF), flavoring agents, preservatives and colorants, and suitable mixtures thereof, as well as any other conventional additive that may be considered by a person skilled in the art practising the present invention, can be found in "Handbook of Pharmaceutical Excipients"; Ed, A. H. Kibbe, 3$^{rd}$ Ed., American Pharmaceutical Association, USA and Pharmaceutical Press UK, 2000, the teachings of which are incorporated herein by reference. As an example, also applicable in the practising of the present invention, it can be mentioned that typical amounts of lubricants and binders are in the order of less than 6 percent by weight of the pharmaceutical composition.

As used herein, the expression oligosaccharide relates to a chain, with any degree of branching, of from three to ten monosaccharide units linked via glycoside bonds. Accordingly, as used herein, the expression polysaccharide relates to a chain, with any degree of branching, of at least eleven monosaccharide units linked via glycoside bonds. Synthetically modified derivatives and analogues of naturally occurring saccharides are also possible to use in the practising of the present invention.

In the marketed tablet resulting from the hitherto used manufacturing process, the lactose particles (Pharmatose 150M provided by DMV, the Netherlands) have an average size of about 50 µm, as determined by an air jet sieve (provided by Alpine GmbH, DE). That particle size does not provide a granulate that allows a compressing speed exceeding about 170 000 tablets per hour (h). In contrast thereto, the process according to the present invention allows a compressing speed of up to about 250 000 tablets/h with the desired tablet quality and retained low level of wear on the tabletting machinery.

As further examples of an upper limit for said average particle size mention can be made of 900, 800, 700 and 600 µm. However, in a preferred embodiment of said pharmaceutical composition, said average particle size is in the range of from 70 to 500 µm. In another preferred embodiment, said average particle size is in the range of from 75 to 350 µm. In yet another preferred embodiment, said average particle size is in the range of from 100 to 200 µm. In a further preferred embodiment, said average particle size is in the range of from 120 to 180 µm. In the most preferred embodiment of the present invention, said average particle size is 140 μm (as measured by an air jet sieve). The lactose particles sold as Pharmatose DCL 15, marketed by DMV in the Netherlands, are of this most preferred average particle size. Other particular embodiments may involve use of e.g. Pharmatose DCL 11, Pharmatose DCL 21 and Pharmatose DCL 40, all provided by the aforementioned DMV, which have an average particle size of 110, 150 and 165 μm, respectively.

According to the commercial provider the particle size distribution of Pharmatose DCL 15 is that essentially all particles have a size below 500 μm, whereas approximately 72% of the particles have a size of from 75 to 350 μm.

In an air jet sieve measurement of particle size, air is drawn upwards, through a sieve, from a rotating slit so that material on the sieve is fluidised. At the same time a negative pressure is applied to the bottom of the sieve which removes fine particles to a collecting device. Size analyses and determination of average particle size are performed by removal of particles from the fine end of the size distribution by using single sieves consecutively. See also "*Particle Size Measurement*", $5^{th}$ Ed., p 178, vol. 1; T. Allen, Chapman & Hall, London, UK, 1997, for more details on this. For a person skilled in the art, the size measurement as such is thus of conventional character.

Accordingly, it is preferred that said substance is a disaccharide, preferably lactose, and more preferably lactose-α-monohydrate.

As said polysaccharide, starch is preferred, and of the many available starches, potato starch is the most preferred. As examples of potato starches mention can be made of Pharma M20, Pharma M14 (provided by KMC, DK) and AmylSolVät (provided by Lyckeby Stärkelse AB, SE).

In a preferred embodiment, both said disaccharide and polysaccharide are present in the pharmaceutical composition. In that particular embodiment, the weight ratio between said disaccharide and polysaccharide is typically from 100:1 to 1:100, preferably from 10:1 to 1:10, and more preferably from 2:1 to 1:2.

The total combined amount of said excipient, diluent and carrier is usually from 5 to 99, preferably from 50 to 99, percent by weight of the pharmaceutical composition, the balance up to 100% being the therapeutically active ingredient optionally together with the aforementioned additives, where the latter is preferably lubricant and binder.

The pharmaceutical composition as a solid dosage form according to the present invention is typically a perorally available tablet. As an alternative non-limiting embodiment, the said tablet may be adapted for oral, including buccal and/or sublingual, administration.

The composition typically comprises desmopressin acetate in an amount of from 20 to 600 μg per unit of solid dosage form. As an example, a typical tablet containing 100 μg of desmopressin acetate is white, convex and oval (6.7×9.5 mm) with a thickness of 3–4 mm and a weight of 200 mg. As another example, a tablet containing 200 μg of desmopressin acetate is white, round (8 mm diameter) and convex with a thickness of 3–4 mm and a weight of 200 mg.

Accordingly, a further aspect of the present invention relates to a method for the manufacturing of a pharmaceutical composition as a solid dosage form comprising desmopressin, or a pharmaceutically acceptable salt thereof, as a therapeutically active ingredient, wherein said method comprises the steps of:
i) mixing desmopressin and an excipient, diluent or carrier, or mixture thereof, optionally in the presence of a wetting agent, wherein at least one of said excipient, diluent and carrier is a substance selected from a monosaccharide, disaccharide, oligosaccharide and a polysaccharide, wherein said substance has an average particle size in the range of from 60 to 1,000 μm;
ii) subjecting the resulting mixture to formation of a granulate, optionally in the presence of a wetting agent, suitable for compression into said solid dosage form;
iii) optionally performing said mixing and/or formation of a granulate in the presence of at least one additive selected from a disintegrating agent, lubricant, binder, flavoring agent, preservative, colorant and a mixture thereof;
iv) optionally drying said granulate;
v) compressing said granulate into said solid dosage form.

The method according to the present invention can as such, once the specific components are identified and included, be practised by using conventional equipment for the manufacturing of pharmaceutical formulations. A granulate suitable for compression into tablets typically has an average granulate size of at least about 100 μm. Discrete granules with a size above 2 mm are usually not transferred to the subsequent compressing step.

As non-limiting examples mention can be made of the following equipment for granulation: directly heated fluidised solid beds e.g. provided by GEA/Collette NV, BE (UltimaPro™ series), Hüttlin GmbH, DE (HDG series), Diosna Dierks & Soehne GmbH, DE (VAC series), Fluid Air Inc., US (Magnaflo® series) and Vector Corp., US (GMX series); indirect conduction moving solids bed, including paddle systems, rotary systems and agitation systems, which are e.g. provided by Jaygo Inc., US (JRB and Novamix series), Paul O. Abbé Inc., US (Rota-Cone, Rota-U, Rota Blade, Cylindrical Ribbon/Paddle, Plow and Sigma-blade series), Forberg A/S, NO (Forberg II series), Gemco Inc., US (D/3 Double Cone, v-Shape and Slant-Cone series), LittlefordDay Inc., US (Double Arm, Day Nauta and Daymax series), Patterson-Kelly, Harsco Corp., US (P-K Solids Processor® series), Diosna as above (CCS and VAC series), Romaco Zanchetta SpA, IT (Rote E, Roto D and Roto P series) and L. B. Bohle Maschinen und Verfahren GmbH, DE (Granumator GMA and Vagumator VMA series); The aforementioned equipment in general also provides drying of the prepared granules.

As indicated above, further examples of an upper limit for said average particle size are 900, 800, 700 and 600 μm. In a preferred embodiment of the method of the present invention, said average particle size is in the range of from 70 to 500 μm. In another preferred embodiment, said average particle size is in the range of from 75 to 350 μm. In yet another preferred embodiment, said average particle size is in the range of from 100 to 200 μm. In a further preferred embodiment, said average particle size is in the range of from 120 to 180 μm. In the most preferred embodiment of the present invention, said average particle size is 140 μm. The lactose particles sold as Pharmatose DCL 15, marketed by DMV in the Netherlands, are of this most preferred average particle size. Other possible embodiments of the present method may involve the aforementioned variants of Pharmatose DCL (vide supra).

It is accordingly preferred that said substance is a disaccharide, preferably lactose, and more preferably lactose-α-monohydrate. Said monosaccharide may also be D-mannitol, D-sorbitol or xylitol or a mixture thereof.

Said polysaccharide is preferably a starch, and more preferably potato starch. Preferred particular potato starches are the same as those mentioned above.

In the method according to the present invention, the manufactured solid dosage form is typically a perorally available tablet. Where desired, it may also be in a form and/or composition adapted for oromucosal administration. Preferred examples of the latter are buccal and/or sublingual administration. Examples of tablet compressing equipment suitable for the practising of the present invention are rotary presses provided by Elizabeth-Hata International, US (HT series), Courtoy Nev., BE (R090F, R100M, R190FT, R290FT, R292F and R233 series), Vector Corp., US (2000, 200 and Magna series), Fette GmbH, DE (Hightech, Medium, Special and WIP series), Manesty, UK (Xpress, Diamond and Value series) and Kilian & Co. GmbH, DE (S, T, E, RX and KTS series).

In a preferred embodiment of the present inventive method said steps of mixing and formation of granulate are performed in a single integrated machinery that is adapted for such a "one-pot", i.e. combined, process. An example of such integrated machinery, alternatively denoted one-pot (single pot) equipment, is the FT series, provided by Forberg A/S, Norway.

It is preferred that where used, said wetting agent is selected from water and a mixture of water and an alcohol, preferably ethanol. A water/ethanol 1:3 mixture is typically used, albeit many other combinations are also possible.

As indicated above, it is preferred that said resulting mixture is subjected to formation of a granulate with an average granulate size of a least 100 μm, preferably in the range of from 100 μm to 2 mm.

In a preferred embodiment of the method, both said disaccharide and polysaccharide are present in the mixing step. The weight ratio between said disaccharide and polysaccharide is then typically from 100:1 to 1:100, preferably from 10:1 to 1:10, and more preferably from 2:1 to 1:2.

The method is preferably performed in such a manner that the total combined amount of said excipient, diluent and carrier is from 5 to 99, preferably from 50 to 99, percent by weight of the pharmaceutical composition.

In the most preferred embodiment, desmopressin acetate is used and mixed with said excipient, diluent and/or carrier in an amount that eventually provides from 20 to 600 μg of desmopressin acetate per unit of solid dosage form (see above and the experimental part for examples of a tablet).

In a further aspect, the present invention also relates to a pharmaceutical composition as a solid dosage form that is obtainable by the novel method as defined above, both in general and as outlined in the specific embodiments.

In order to substantiate and illustrate the present invention in more detail, the following example is provided. It shall not be construed as a limitation of how the invention may be practised.

EXAMPLE

Example 1

Preparation of Solid Dosage Form of dDAVP

Desmopressin acetate (100 or 200 g; provided by PolyPeptide Laboratories AB, SE), polyvinyl pyrrolidone (PVP) as binder (1.84 kg; Kollidon® 25 provided by BASF GmbH, DE) and granulation liquid (water/ethanol 1:3 mixture) are combined in a vessel and mixed at room temperature until a clear solution is achieved. The potato starch (77 kg, average particle size about 40–50 μm according to laser diffraction measurements; AmylSolVät provided by Lyckeby Stärkelse AB, SE), is weighed and sieved through a 2 mm sieve. Lactose (120 kg, DCL 15 provided by DMV NV, NL; see above for the details of this product) is weighed and loaded together with the starch into a single pot mixer (FT-350; provided by Forberg A/S, NO) and mixed therein. The granulation liquid solution is then sprayed onto the powder mixture, after which the moist granulate is dried with warm air (150° C.), all with continued mixing. The dried granulate is then sieved (2 mm) and transferred to a double cone mixer. Magnesium stearate (max 1.0 kg; provided by Peter Greven NV, NL) is then weighed in, sieved (1 mm) and transferred to the double cone mixer for final mixing. Tablets are then compressed from the resulting mixture by using a conventional rotary tablet compression machine (Kilian S-250), whereby a compressing speed of about 250 000 tablets/h is attainable with adequate tablet quality and low machine wear. A tablet of adequate quality has a smooth surface without scratches or chipped edges, and it shows no tendencies to lamination (so-called capping).

The process is typically adapted to provide a tablet containing 100 or 200 μg of desmopressin acetate with the aforementioned appearance, dimension and weight.

What is claimed is:

1. A method for manufacturing a pharmaceutical composition as a solid dosage form comprising desmopressin acetate, as a therapeutically active ingredient, wherein said method comprises the steps of:
   i) mixing desmopressin acetate and an excipient, diluent or carrier, or mixture thereof, optionally in the presence of a wetting agent, wherein at least one of said excipient, diluent and carrier is a disaccharide, wherein said disaccharide has an average particle size in the range of from 70 to 500 μm;
   ii) subjecting the resulting mixture to formation of a granulate, optionally in the presence of a wetting agent, suitable for compression into said solid dosage form;
   iii) optionally performing said mixing and/or formation of a granulate in the presence of at least one additive selected from a disintegrating agent, lubricant, binder, flavoring agent, preservative, colorant and a mixture thereof;
   iv) optionally drying said granulate;
   v) compressing said granulate into said solid dosage form, wherein said solid dosage form is a tablet.

2. The method according to claim 1, wherein said average particle size is in the range of from 75 to 350 μm.

3. The method according to claim 2, wherein said average particle size is in the range of from 100 to 200 μm.

4. The method according to claim 3, wherein said average particle size is in the range of from 120 to 180 μm.

5. The method according to claim 1, wherein said disaccharide is lactose.

6. The method according to claim 1, wherein said steps of mixing and formation of a granulate are performed in a single integrated machinery that is adapted for such a combined process.

7. The method according to claim 1, wherein said wetting agent is selected from water and a mixture of water and an alcohol.

8. The method according to claim 1, wherein said resulting mixture is subjected to formation of a granulate with an average granulate size of a least 100 μm.

9. The method according to claim 1, wherein the total combined amount of said excipient, diluent and carrier is from 5 to 99 percent by weight of the pharmaceutical composition.

10. The method according to claim 1, wherein desmopressin acetate is used and mixed with the excipient, diluent or carrier in an amount that provides from 20 to 600 μg of desmopressin acetate per unit of solid dosage form.

11. The method according to claim 1, wherein said tablet is adapted for administration by a route selected from the group consisting of oromucosal, buccal and sublingual administration.

12. The method according to claim 5, wherein said lactose is lactose-α-monohydrate.

13. The method according to claim 7, wherein said alcohol is ethanol.

14. The method according to claim 9, wherein the total combined amount of said excipient, diluent and carrier is from 50 to 99 percent by weight of the pharmaceutical composition.

15. The method according to claim 8, wherein said resulting mixture is subjected to formation of a granulate with an average granulate size of from 100 μm to 2 mm.

* * * * *